US008176916B2

(12) United States Patent
Pedarzini et al.

(10) Patent No.: US 8,176,916 B2
(45) Date of Patent: May 15, 2012

(54) FILTER AND/OR HME DEVICE FOR RESPIRATORY CIRCUITS COMPRISING A CONDENSATION TRAP

(75) Inventors: Alessandra Pedarzini, Finale Emilia (IT); Stefano Tralli, Felonica (IT); Marco Lodi, Mirandola (IT)

(73) Assignee: Covidien AG, Neuhausen am Rheinfall (CH)

( * ) Notice: Subject to any disclaimer, the term of this patent is extended or adjusted under 35 U.S.C. 154(b) by 526 days.

(21) Appl. No.: 12/465,271

(22) Filed: May 13, 2009

(65) Prior Publication Data
US 2009/0301479 A1 Dec. 10, 2009

(30) Foreign Application Priority Data

Jun. 10, 2008 (EP) .................................... 08425409

(51) Int. Cl.
*A61M 16/00* (2006.01)
(52) U.S. Cl. .......... 128/205.12; 128/203.12; 128/205.27
(58) Field of Classification Search .......... 128/207.14–207.16, 205.12, 203.12, 128/205.27
See application file for complete search history.

(56) References Cited

U.S. PATENT DOCUMENTS

| | | | | |
|---|---|---|---|---|
| 3,454,005 A | * | 7/1969 | Eubanks et al. | 128/203.12 |
| 4,172,709 A | * | 10/1979 | Kippel et al. | 96/416 |
| 4,327,718 A | * | 5/1982 | Cronenberg | 128/205.12 |
| 4,457,305 A | * | 7/1984 | Shanks et al. | 128/205.12 |
| 5,168,868 A | * | 12/1992 | Hicks | 128/205.12 |
| 5,826,575 A | | 10/1998 | Lall | |
| D527,107 S | * | 8/2006 | Baker et al. | D24/164 |

FOREIGN PATENT DOCUMENTS

| | | |
|---|---|---|
| EP | 0 413 127 A2 | 2/1991 |
| EP | 1 342 485 A1 | 9/2003 |
| WO | WO 91/05579 A1 | 5/1991 |
| WO | WO 01/02034 A2 | 1/2001 |
| WO | WO 2005/115520 A1 | 12/2005 |

OTHER PUBLICATIONS

European Office Action for Appln. No. 08425409.3 dated May 27, 2010.
European Search Report for EP Application No. EP 08 42 5409 completed Nov. 27, 2008.

\* cited by examiner

*Primary Examiner* — Stephen Crow
(74) *Attorney, Agent, or Firm* — Carter, DeLuca, Farrell & Schmidt LLP

(57) ABSTRACT

A filter and/or HME device including an upper shell suitable to be connected to ventilation means, a lower shell suitable to be connected to a tracheal or tracheostomy tube of a patient, a filter and/or HME element disposed between the upper shell and the lower shell and a condensation screen disposed in front of the filter and/or HME element and facing the lower shell wherein the condensation screen has a conical wall extending from the opposite part of the filter and/or HME element to produce, together with a portion of the lower shell a collection chamber for the condensation that forms.

9 Claims, 2 Drawing Sheets

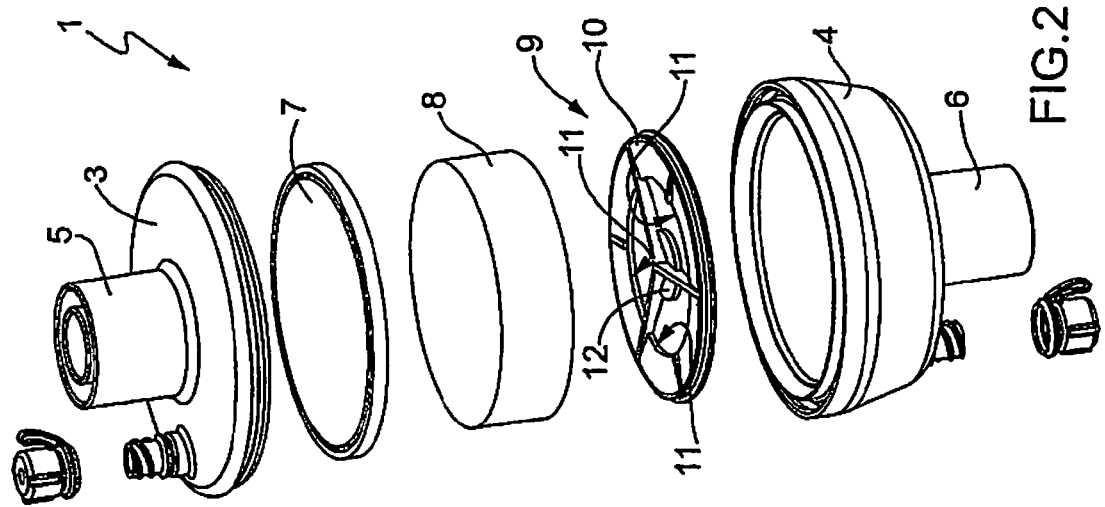
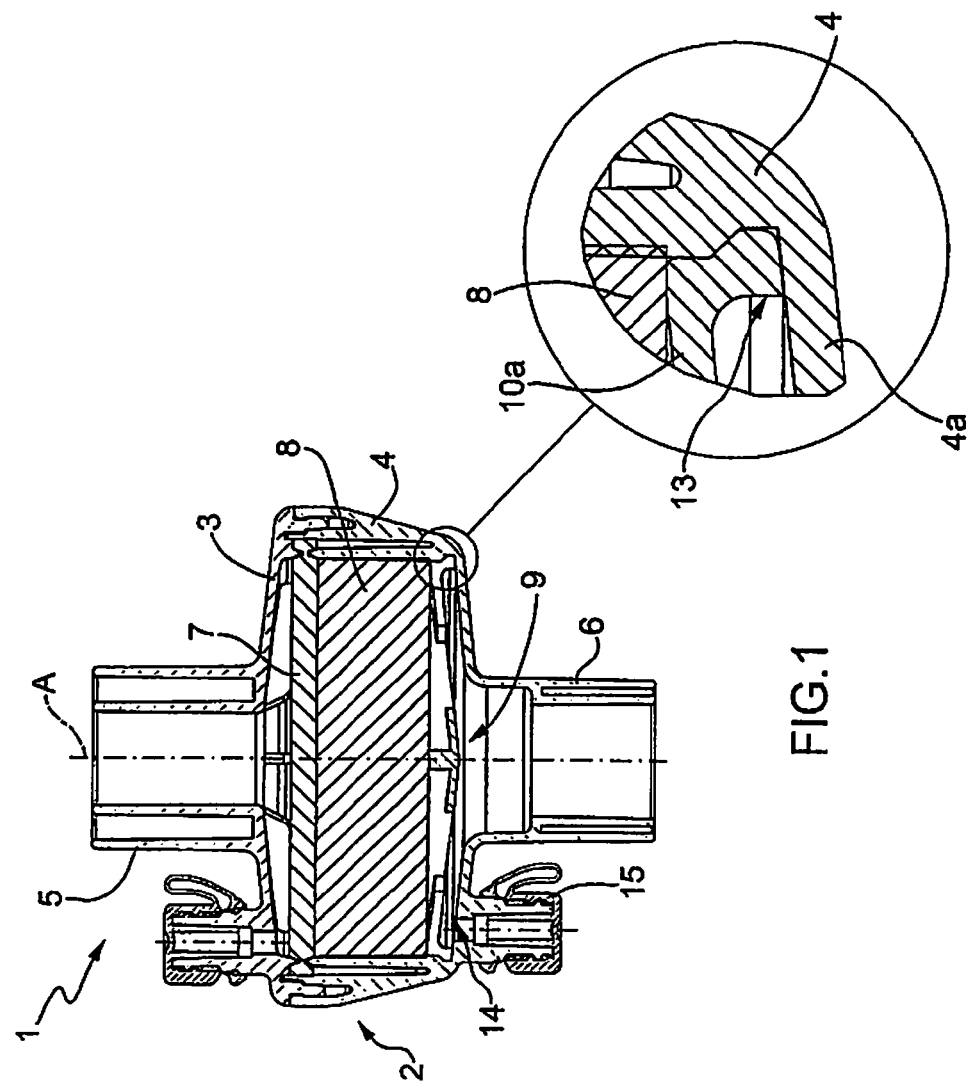

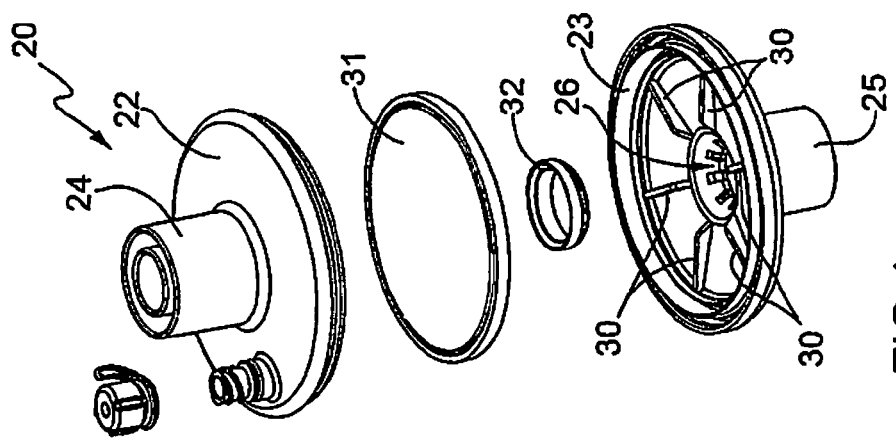
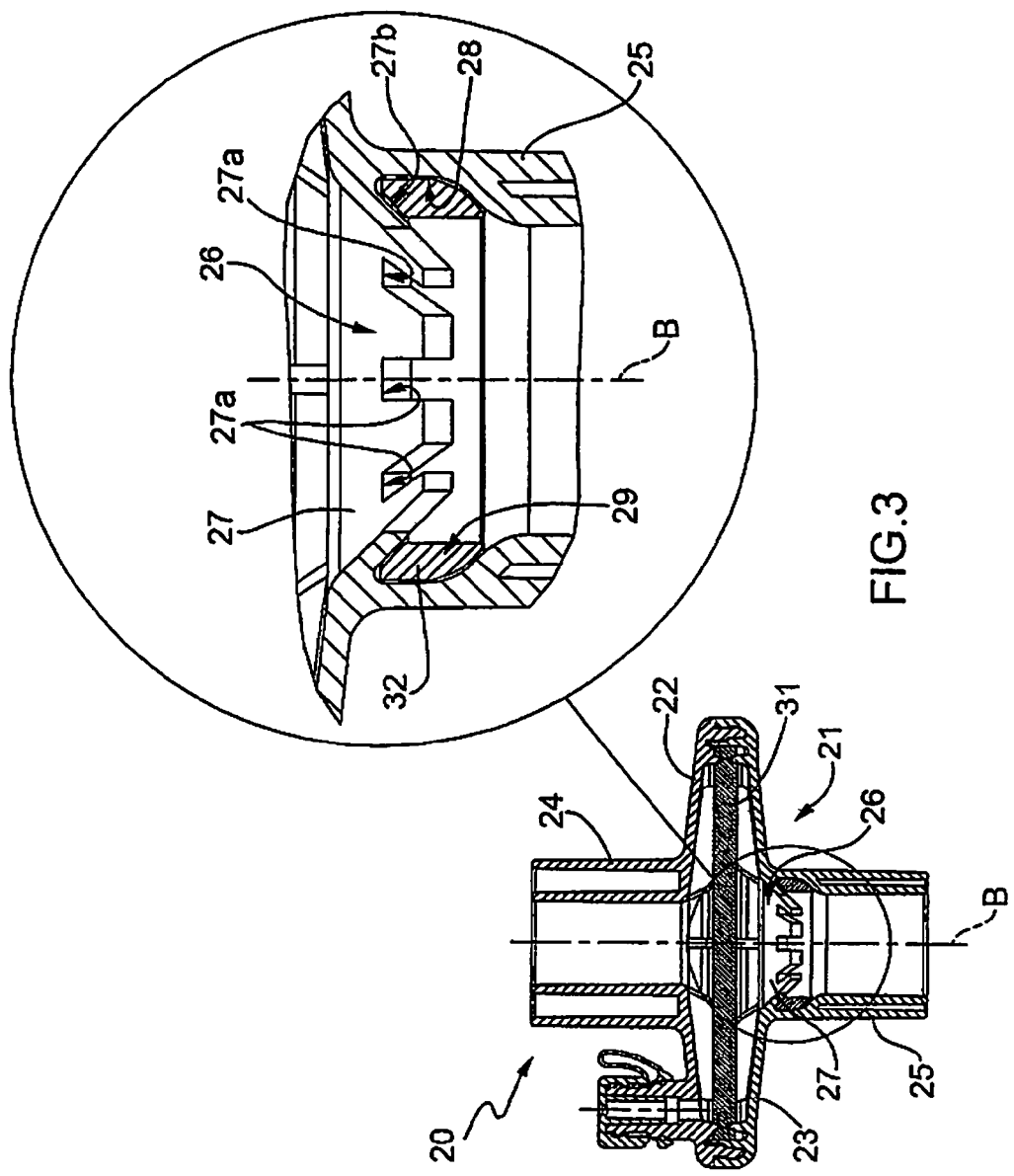
FIG.3
FIG.4

FILTER AND/OR HME DEVICE FOR RESPIRATORY CIRCUITS COMPRISING A CONDENSATION TRAP

TECHNICAL FIELD

The present disclosure relates to a filter and/or HME device for respiratory circuits having a condensation trap.

BACKGROUND

As it is known, respiratory circuits, which are used to interface in a flexible manner the tracheal or tracheostomy tube of a patient with a ventilation system, comprise filter and HME (Heat Moisture Exchanger) devices in order to ensure that the quality, temperature and humidity of the air inhaled by the patient are such that they have no negative effects on the patient. HME devices are suitable to retain water vapour coming from the air exhaled by the patient and to use it to humidify the air coming from the ventilation system and which will be inhaled by the patient.

A drawback that can occur during use of respiratory circuits concerns the formation of condensation coming from humidity in the air exhaled by the patient. In fact, the air exhaled is at a higher temperature and when it reaches the filter and/or HME device, it encounters a lower temperature which can cause the formation of condensation of the water vapour with which it is saturated.

As may be apparent, the formation of this condensation can compromise correct operation of the filter and/or HME device, at least partially obstructing the passage of air, with the consequence that this filter and/or HME device must be replaced, with the problems in terms of cost and practicality that this implies.

SUMMARY

The object of the present disclosure is to produce a filter and/or HME device having a condensation trap capable of overcoming the aforesaid drawbacks.

In accordance with the present disclosure, a filter and/or HME device is presented which includes an upper shell suitable to be connected to a ventilation means, a lower shell suitable to be connected to a tracheal or tracheostomy tube, a filter and/or HME disposed between the upper shell and the lower shell; and a condensation screen disposed in front of the filter and/or HME and facing the lower shell; the condensation screen having a conical wall extending away from the filter and/or HME and suitable to produce, together with a portion of the lower shell a collection chamber for the condensation that forms; and wherein the condensation screen presents a plurality of openings disposed about an axis of symmetry of the conical wall.

BRIEF DESCRIPTION OF THE DRAWINGS

The figures below are provided purely as non-limiting examples, to facilitate comprehension of the disclosure with the aid of the figures of the accompanying drawing, in which:

FIG. 1 shows a section of the device forming the object of the present disclosure according to a first embodiment;

FIG. 2 shows an exploded view of the device of FIG. 1;

FIG. 3 shows a section of the device of the present disclosure according to a second embodiment; and FIG. 4 shows an exploded view of the device of FIG. 3.

DETAILED DESCRIPTION

The present disclosure relates to a filter and/or HME device including an upper shell suitable to be connected to ventilation means, a lower shell suitable to be connected to a tracheal or tracheostomy tube of a patient, a filter and/or HME element disposed between the upper shell and the lower shell and a condensation screen disposed in front of the filter and/or HME element and facing the lower shell; the condensation screen having a conical wall extending from the opposite part of the filter and/or HME element and suitable to produce, together with a portion of the lower shell, a collection chamber for the condensation that forms; wherein the condensation screen presents a plurality of openings disposed about an axis of symmetry of the conical wall.

According to an embodiment, the device of the present disclosure includes a drainage opening facing the condensation collection chamber.

According to a further embodiment of the device of the present disclosure, the lower shell includes a connection duct suitable to connect with the tracheal or tracheostomy tube; the condensation screen is produced in one piece with the lower shell and extends in the shape of a funnel inside the connection duct. Preferably, in this embodiment, the openings produced in the condensation screen are connected to one another at the axis of symmetry from which they extend radially.

In embodiments, as illustrated by FIGS. 1 and 2, the device 1 includes a containing structure 2 composed of an upper shell 3 and a lower shell 4 coupled to each other with an interlocking mechanism. Both shells 3 and 4 are provided with respective connection ducts 5 and 6, suitable to be connected respectively and indirectly with ventilation means and with the tracheal or tracheostomy tube of a patient.

Inside the containing structure there are housed, from top to bottom, a filter 7, an HME 8 and a condensation screen 9. In embodiments, the condensation screen 9 is disposed between the HME element 8 and a bottom wall 4a of the lower shell 4.

The condensation screen 9 is defined by a conical wall 10, produced in which are three openings 11 are disposed around a central portion 12, passing through an axis of symmetry A of the wall 10. The conical shape of the wall 10 determines a collection chamber 13 for the condensation that forms, defined by a peripheral portion 10a of the wall 10 and by the bottom wall 4a of the lower shell 4.

In the bottom wall 4a of the lower shell 4 there is produced a drainage opening 14, facing the collection chamber 13 and connected to a drainage outlet 15. The function of the drainage opening 14 and of the drainage outlet 15 is to allow the condensation that forms and is present in the collection chamber 13 to be removed from the outside through the use of a syringe or the like.

Finally, the circular shaped central portion 12 of the wall 10 has the function of intercepting any organic fluids exhaled by the patient.

Therefore, the condensation screen 9 prevents the condensation that forms from reaching the filter and/or HME elements, conveying the condensation to the collection chamber 13 while the air flows through the openings 11 and, at the same time, also prevents any organic fluids from reaching the filter and/or HME elements by intercepting these fluids with the central portion 12.

In embodiments, as illustrated by FIGS. 3 and 4, the device 20 includes a containing structure 21 composed of an upper shell 22 and of a lower shell 23 coupled to each other with an interlocking mechanism. Both shells 22 and 23 are provided with respective connection ducts 24 and 25, suitable to be connected respectively and indirectly with ventilation means and with the tracheal or tracheostomy tube of a patient.

The device 20 includes a condensation screen 26 produced in one or more pieces with the lower shell 23 and defined by a wall 27 extending in the shape of a funnel inside the connection duct 25.

In the wall 27 there are produced a plurality of rectangular shaped openings 27A, extending radially from an axis of symmetry B of this wall 27. In the connection duct 25 there is produced a circular recess 28 at the extension of the wall 27 of the condensation screen 26. The circular recess 28 defines, together with the peripheral portion 27b of the wall 27, a collection chamber 29 for the condensation that forms. The shape of the wall 27 conveys the condensation that forms into the collection chamber 29 while the air flows through the openings 27a.

The lower shell 23 also includes a plurality of ribs 30 facing the upper shell 22 and on which there are placed a filter and/or HME 31 housed in the containing structure 21.

Finally, the device 20 includes a ring of absorbent material 32 housed inside the collection chamber 29 to provide a further assurance that the condensation that forms will not reach the filter or HME.

As will be apparent to those skilled in the art, in the absence of the ring of absorbent material 32, the device 20 can be provided with a drainage opening similar to the opening 14 of the device 1, and facing the collection chamber 29.

As described above, the devices of the present disclosure ensure that the condensation that forms does not reach the filter or HME and therefore does not compromise operation thereof and, at the same time, allows condensation to be conveyed to the collection chamber without this requiring disassembly or replacement of the device.

What is claimed is:

1. A filter and/or HME device comprising:
    an upper shell suitable to be connected to ventilation means,
    a lower shell suitable to be connected to a tracheal or tracheostomy tube,
    a filter and/or HME disposed between said upper shell and said lower shell; and
    a condensation screen disposed in front of said filter and/or HME and facing said lower shell;
    said condensation screen having a conical wall extending away from said filter and/or HME and suitable to produce, together with a portion of the lower shell a collection chamber for the condensation that forms; and
    wherein said condensation screen presents a plurality of openings realized in said conical wall and disposed about an axis of symmetry of the conical wall.

2. The filter and/or HME device according to claim 1, wherein said openings are connected to one another at said axis of symmetry from which they extend radially.

3. The filter and/or HME device according to claim 2, wherein said lower shell comprises a connection duct suitable to connect with the tracheal or tracheostomy tube.

4. The filter and/or HME device according to claim 3, wherein said condensation screen is configured in one or more pieces with said lower shell and extending in the shape of a funnel inside said connection duct.

5. The filter and/or HME device according to claim 4, wherein said connection duct includes a circular recess such as to define, together with the peripheral portion of the conical wall, a collection chamber.

6. The filter and/or HME device according to claim 1, wherein said conical wall includes a central portion having said plurality of openings; said central portion configured to intercept any organic fluids exhaled by the patient.

7. The filter and/or HME device according to claim 1, further comprising a drainage opening facing said collection chamber.

8. The filter and/or HME device according to claim 7, wherein the drainage opening is connected to a drainage outlet configured to allow the condensation present in the collection chamber to be removed therefrom.

9. The filter and/or HME device according to claim 1, further comprising a ring of absorbent material housed inside said collection chamber.

* * * * *